(12) United States Patent
Hu et al.

(10) Patent No.: US 7,576,128 B2
(45) Date of Patent: Aug. 18, 2009

(54) ANDROGEN RECEPTOR MODULATORS

(75) Inventors: Lain-Yen Hu, Ann Arbor, MI (US);
Huangshu Lei, Waltham, MA (US);
Daniel Y. Du, Milan, MI (US); Bruce A. Lefker, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 799 days.

(21) Appl. No.: 11/053,010

(22) Filed: Feb. 8, 2005

(65) Prior Publication Data

US 2005/0182132 A1    Aug. 18, 2005

Related U.S. Application Data

(60) Provisional application No. 60/544,738, filed on Feb. 13, 2004, provisional application No. 60/605,647, filed on Aug. 30, 2004.

(51) Int. Cl.
*A61K 31/277* (2006.01)
*C07C 255/49* (2006.01)

(52) U.S. Cl. ...................... 514/524; 558/423

(58) Field of Classification Search ............... 558/423; 514/524
See application file for complete search history.

(56) References Cited

U.S. PATENT DOCUMENTS

| | | | |
|---|---|---|---|
| 3,535,365 A | 10/1970 | Weinstock | |
| 4,029,493 A | 6/1977 | Theissen | |
| 4,234,595 A | 11/1980 | Kreighbaum et al. | |
| 4,263,223 A | 4/1981 | Pauly | |
| 4,536,321 A | 8/1985 | Sugimori et al. | |
| 4,925,590 A | 5/1990 | Reiffenrath | |
| 4,992,433 A | 2/1991 | Stokbroekx et al. | |
| 5,108,652 A | 4/1992 | Eidenshink | |
| 5,316,755 A | 5/1994 | Illig et al. | |
| 5,847,166 A | 12/1998 | Buchwald | |
| 5,910,493 A | 6/1999 | Golbs et al. | |
| 5,990,142 A | 11/1999 | Carganico et al. | 514/382 |
| 6,011,606 A | 1/2000 | Ohe | |
| 6,124,343 A | 9/2000 | Smith | |
| 2003/0175445 A1 | 9/2003 | Kirsch et al. | |
| 2003/0199427 A1 | 10/2003 | Moye-Sherman | |
| 2003/0229129 A1 | 12/2003 | Kraemer et al. | |
| 2003/0232882 A1 | 12/2003 | Miller et al. | |
| 2003/0236304 A1 | 12/2003 | Jolidon | |
| 2004/0006134 A1 | 1/2004 | Labrie | |
| 2006/0009427 A1 | 1/2006 | Hu et al. | |

FOREIGN PATENT DOCUMENTS

| | | |
|---|---|---|
| CN | 1214048 | 4/1999 |
| DE | 2301541 A1 | 1/1972 |
| DE | 3515633 A | 11/1986 |
| DE | 3825170 A1 | 1/1990 |
| DE | 4017019 A1 | 11/1991 |
| DE | 298470 A | 2/1992 |
| DE | 4217928 A1 | 12/1993 |
| DE | 10126434 A | 12/2002 |
| EP | 15505 | 9/1980 |
| EP | 0002309 | 12/1982 |
| EP | 0080371 A | 6/1983 |
| EP | 0119756 | 9/1984 |
| EP | 1348433 A | 4/1985 |
| EP | 0193303 | 9/1986 |
| EP | 221844 A | 5/1987 |
| EP | 100172 B1 | 8/1987 |
| EP | 269383 A | 6/1988 |
| EP | 412814 A | 2/1991 |
| EP | 419286 A | 3/1991 |
| EP | 488474 A1 | 6/1992 |
| EP | 0601977 A | 6/1994 |
| EP | 0609587 A | 8/1994 |
| EP | 0673986 A2 | 3/1995 |
| EP | 654468 A1 | 5/1995 |
| EP | 0684235 A | 11/1995 |
| EP | 0579223 | 10/1996 |
| EP | 0790235 A1 | 8/1997 |
| EP | 1070753 A2 | 1/2001 |
| EP | 1123933 A1 | 8/2001 |
| EP | 0707007 B1 | 12/2001 |
| EP | 1325910 A1 | 7/2003 |
| EP | 1348701 A | 10/2003 |
| GB | 1369696 A | 10/1974 |
| GB | 2278054 A | 11/1994 |
| GB | 2347423 A | 9/2000 |
| JP | 59144747 | 8/1984 |
| JP | 61189243 | 8/1986 |
| JP | 04124183 | 4/1992 |
| JP | 04300877 | 10/1992 |
| JP | 5310616 | 11/1993 |
| JP | 07309850 | 11/1995 |
| JP | 8325154 | 12/1996 |
| JP | 10007647 A | 1/1998 |
| WO | WO9219210 A2 | 11/1992 |
| WO | WO94/05153 A | 3/1994 |
| WO | WO9510521 A1 | 4/1995 |

(Continued)

OTHER PUBLICATIONS

Loeffler L J et al: "Synthesis of Isosteres of P-Amidinophenylpyruvic Acid Inhibitors of Trypsin, Thrombin, and Pancreatic Kallikrein" Mar. 1, 1975, J. Of Med Chem, Amer. Chem. Soc. Wash. pp. 287-292 XP000574801 ISSN: 0022-2623.

(Continued)

*Primary Examiner*—James O Wilson
*Assistant Examiner*—Ebenezer Sackey
(74) *Attorney, Agent, or Firm*—Gregg C. Benson; J. Michael Dixon

(57) ABSTRACT

The present invention is directed to a new class of 4-oxo-benzonitriles, their use as androgen modulators, and to their use in the treatment of alopecia.

11 Claims, 1 Drawing Sheet

FOREIGN PATENT DOCUMENTS

| WO | WO95/28969 | 11/1995 |
|---|---|---|
| WO | 9626921 | 9/1996 |
| WO | WO9735845 A1 | 10/1997 |
| WO | WO98/33779 A | 8/1998 |
| WO | WO99/08673 A | 2/1999 |
| WO | WO9917777 | 4/1999 |
| WO | WO00/37430 | 6/2000 |
| WO | WO0034247 A | 6/2000 |
| WO | WO0034269 A | 6/2000 |
| WO | WO0059888 A | 10/2000 |
| WO | WO01/56989 A2 | 8/2001 |
| WO | WO02/06196 | 1/2002 |
| WO | WO0218333 A | 3/2002 |
| WO | WO0220484 A | 3/2002 |
| WO | WO0236734 A | 5/2002 |
| WO | WO0241889 A | 5/2002 |
| WO | WO02/057215 A | 7/2002 |
| WO | WO02060896 A | 8/2002 |
| WO | WO02070484 A | 9/2002 |
| WO | WO02/085860 | 10/2002 |
| WO | WO02/090332 A2 | 11/2002 |
| WO | WO03065992 A | 8/2003 |
| WO | WO03066632 A | 8/2003 |
| WO | WO03068217 A | 8/2003 |
| WO | WO03068754 | 8/2003 |
| WO | WO03/074473 A | 9/2003 |
| WO | WO03082787 | 10/2003 |
| WO | WO03093243 | 11/2003 |
| WO | WO2004/018386 A | 3/2004 |
| WO | WO2004/018477 A2 | 3/2004 |
| WO | WO2004110994 A1 | 12/2004 |
| WO | WO2005000794 | 1/2005 |
| WO | WO2005013914 A | 2/2005 |
| WO | WO2005042464 A1 | 5/2005 |
| WO | WO2005/049574 | 6/2005 |
| WO | WO2005080320 A1 | 9/2005 |
| WO | WO2005/100305 A | 10/2005 |
| WO | WO2005/102990 A | 11/2005 |
| WO | WO2005/108361 | 11/2005 |
| WO | WO2005102990 | 11/2005 |
| WO | WO2006006065 | 1/2006 |
| WO | WO2006018723 A2 | 2/2006 |
| WO | WO2006018732 A | 2/2006 |
| WO | WO2006024942 | 3/2006 |
| WO | WO2006/049952 | 5/2006 |
| WO | 2006136910 | * 12/2006 |

OTHER PUBLICATIONS

Database Caplus Online Chemical Abstracts Service, Columbus, Ohio US Berg, S.S. et al., chemotherapeutic amidines X. Substituted 4.4'-diamidino-omega, omega.-diphenoxyalkanes and diphenyl ethers XP002333841 retrieved from STN Database accession No. 1949:50548 abstract & Journal of the Chemical Society Abstracts, 1949, pp. 642-648.

Database Caplus Online Chemical Abstracts Service, Columbus, Ohio US Kratzl. K. et al: "Chemistry of vanillin and its derivatives X. Amidines imidazolines and tetrahydropyrimidinediones with quaiacol substituents" XP002333842 Retrieved from STN Database accession No. 1958:65868 abstract & Monatshefte Fuer Chemie, 88, 1957, pp. 1056-1063.

Database Caplus Online Chemical Abstracts Service, Columbus, Ohio US Davis, M.: "Search for chemotherapeutic amidines. XV. 2-Methoxy and 2-hydroxy derivatives of 1,5-bis(p-amidinophenoxy) pentane" XP002333843 retrieved from STN Database accession No. 1958:82447 abstract & Journal of the Chemical Society, Abstracts. 1958, pp. 907-908.

Data Base CA Online Chemical Abstracts Service, Columbus, Ohio, US; Ferroni, R. Et al., "Aromatic tetra- amidines: synthesis of halo-derivatives and their antiproteolytic activity" XP002333844 retrieved from STN Database accession No. 1985:91904 abstract & Farmaco, Edizione Scientifica, vol. 39, No. 11, 1984, pp. 901-909.

Data Base Caplus Online Chemical Abstracts Service, Columbus, Ohio US Leznoff, Clifford C et al: "Metallophthalocyanine dimers incorporating five-atom covalent bridges" XP002333845 retrived from STN Databse accession No. 1985:447150 abstract & Canadian Journal of Chemistry vol. 63. No. 3, 1985, pp. 623-631.

Data Base Caplus Online Chemical Abstracts Service, Columbus, Ohio US Woehrle Dieter et al.: "Polymeric phthalocyanines and their precursors 15. Syntheses of alkylenedioxy-bridged polymeric phthalocyanines and their absorption capacities for organic solvents in comparison to other phthalocyanines" XP002333846 retrieved from STN Database accession No. 1988:493734 abstract & Makromolekulare Chemie, vol. 189, No. 6, 1988, pp. 1229-1238.

Geratz J.D. et al: "Diamidino-alpha.. omega.-diphenoxyalkane s. Structure-activity relations for the inhibition of thrombin, pancreatic kallikrein, and trypsin" Journal of Medicinal Chemistry, vol. 16, No. 9, 1973, pp. 970-975, XP002333840 table VI, compounds 27-30, 32-34, 37.

Database Caplus Online Chemical Abstracts Service, Columbus, Ohio US, Csokai, Viktor et al: "Microwave-assisted synthesis of phtalonitriles and phthalocyanines"XP002333847 retrieved from STN Database accession No. 2003:416216 abstract & Synthetic Communications, vol. 33, No. 10, 2003, pp. 1615-1621.

Database Caplus, Online Chemical Abstracts Service, Columbus, Ohio, US: Eastmond, G.C. et al: "Polyimides with main-chain ethylene oxide units:synthesis and properties" retrieved from STN Database accession No. 2002:264464 abstract & Polymer, vol. 43, No. 12, 2002, pp. 3455-3468.

Database Caplus, Online Chemical Abstracts Service, Columbus, Ohio, US; Zhang, Yisheng et al: "Tetranuclear Hexanuclear, and Octanuclear Copper (II) Complexes of a Series of Novel Dendritic Poly(phthalazine) Ligands" XP002333849 retrieved from STN Database accession No. 1995:875232 abstract & Inorganic Chemistry, vol. 34, No. 23, 1995, pp. 5870-5877.

Database Caplus, Online Chemical Abstracts Service, Columbus, Ohio, US: Kobayashi, Nagao et al: "Optically active phthalocyanines and their circular dichroism" XP002333850 retrieved from STN Database accession No. 1993:652129 abstract & Journal of the American Chemical Society, vol. 115, No. 23, 1993, pp. 10994-10995.

Database Caplus, Online Chemical Abstracts Service, Columbus, Ohio, US; Keller, Teddy M. et al: "Synthesis of phthalonitriles by nitro displacement" XP002333851 retrieved from STN Database accession No. 1981:442589 abstract & Synthesis, No. 8. 1980, p. 613.

Database Caplus, Online Chemical Abstracts Service, Columbus, Ohio, US: Dann, Otto et al: "Syntheses of biscationi, trypanocidal 1-benzofuran compounds" XP002333852 retrieved from STN Database accession No. 1983:53580 abstract & Liebigs Annalen Der Chemie, No. 1982, pp. 1836.

FR 2397387A (Laboratoires Serobiologiques SA) Feb. 9, 1979 p. 4, line 4-line 10; claim 12; example III (US4263223 US equivalent).

Shankar M. Singh et al: Androgen Receptor Antagonists (Antiandrogens):Structuro-Activity Relationships, Current Medicinal Chemistyr, 2000, 7 pp. 211-247.

Bohl, Casey E., et al, Structural basis for antagonism and resistance of bicalutamide in prostate cancer, PNAS, Apr. 26, 2005, vol. 102, No. 17 pp. 6201-6206.

Abstract:: Arnold, Donald R. et al., Radical ions in photochemistry. Part 20. The photochemical nucleophile-olefin combination, aromatic substitution reaction. Canadian Journal of Chemistry (1988) 66 (12), 3012-26.

Gregorio Asensio et al., Synthesis of an enantiopure 2-arylcyclohexanols form prochiral enol acetates by an enantioselective protonation/diastereoselective reduction sequence, Tetrahedron: Asymmetry 14(2003) 3851-3855.

Alexandre Alexakis et al., Enantioselective Nucleophilic Opening fo meso Epoxides by Organolithium Reagents, Synlett Oct. 1998, pp. 1165-1167.

Micropatent English Abstract of Japanese Patent (JP2001-247411).
Derwent English Abstract of German Patent Application (DE3939116A1).

Related United States Co-pending U.S. Appl. No. 11/175,097, filed Jul. 5, 2005, now published as 2006-0009427A1 on Jan. 12, 2006.

Palucki, M. et al., "Palladium-catalyzed intermolecular carbon-oxygen bond formation, A new sysnthesis of aryl ethers". J. Am. Chem. Soc., 1997, vol. 119, nr. 14, pp. 3395-3396.

Database CA [Online] Chemical Abstracts Service, Columbus, Ohio, US; Yasuda, Kosuke et al: "Preparation of aliphatic nitrogenons five-membered ring compounds as dipeptidyl peptidase TV inhibitors" XP002350473 retrived from STN Database accession No. 136:325560.

Database CA [Online] Chemical Abstracts Service, Columbus, Ohio, US; Chaki, Hisaaki et al: "Preparation and formulation of alkylsulfonylbiphenyl and aminosulfonylbiphenyl derivatives as selective COX-2 inhibitors" XP002350472 retrieved from STN Database accession No. 125:300608.

Patent Abstracts of Japan vol. 013, No. 021 (C-560), Jan. 18, 1989 & JP 63227502A (SDS Biotech KK), Sep. 21, 1988.

Reiling B A et al.: "Effect of prenatal androgenization on performance, lactation, carcass, and sensory traits of heifers in a single-calf heifer system" Journal of Animal Science, vol. 73, No. 4, 1995, pp. 986-992, XP0088065209 ISSN: 0021-8812.

Heitzman R J: "The effectiveness of anabolic agents in increasing rate of growth in farm animals; report on experiments in cattle." Environmental, Quality and Safety, Supplement, 1976, No. 5, 1976, pp. 89-98, XP008065222 ISSN: 0340-4714.

Botzki, Salmen: "Structure based design . . . " Cominatorial Science, vol. 24, No. 4, 2005, pp. 458-469, XP008065218.

Database VA Online Chemical Abstracts Service, Columbus Ohio US; Chang, Chih-Shiang et al.: "Design and synthesis of 1, 2, 4-oxadiazole derivatives as non-steroidal 5 alpha.-reductase inhibitors" XP002419614 retreived from STN & Journal of the Chinese Chemical Society (Taipei, Taiwan), 49(1), 83-89 Coden: JCCTAC; ISSN: 00904536, 2002.

Database VA Online Chemical Abstracts Service, Columbus Ohio US; Ashley, J.N. et al: "Chemotherapeutic Comparison of the trypanocidal action of some aromatic diamidines" XP002419615 retrieved from STN Database accession No. 1942:22799 abstract & Journal of the Chemical Society 103-16 Coden: JCSOA9; ISSN: 0368-1769, 1942.

Database VA Online Chemical Abstracts Service, Columbus Ohio US; Dol Fuminao et al: "Synthesis of chroman derivatives by the ring expansion reaction of spirodienones, and an assessment of their plant growth inhibition" XP002419616 retrived from STN Database accession No. 2004:1127989 abstract & Bullentin of the Chemical Society of Japan, 77(12), 2257-2263, Coden: BCSJA8; ISSN: 009-2673.

Kuwabe, S., et al., Palladium-Catalized Intramolecular C-O Bond Formation; *J. Am. Chem. Soc.*, 2001, 123: 12202-12206.

Qian, et al., *J. Chem. Tech, Biotechnol.*, vol. 67, pp. 124-130 (1996).

Wagner, et al., *Tetrahedron Letters*, vol. 43, pp. 3569-3571 (2002).

Co-pending commonly assigned. U.S. Appl. No. 11/415,935, filed May 2, 2006, now published as 2006-0252796A1, on Nov. 9, 2006.

Co-pending commonly assigned. U.S. Appl. No. 11/572,743, filed Aug. 5, 2005, now published as 2008-0064745A1, on Mar. 13, 2008.

Co-pending commonly assigned. U.S. Appl. No. 11/572,143, filed Apr. 1, 2005, now published as 2007-0197641A1, on Aug. 23, 2007.

Co-pending commonly assigned. U.S. Appl. No. 10/599,719, filed Apr. 14, 2005, now published as 2007-0197642A1, on Aug. 23, 2007.

Co-pending commonly assigned. U.S. Appl. No. 11/997,983, filed Jul. 27, 2006.

Co-pending commonly assigned. U.S. Appl. No. 11/572,760, filed Aug. 8, 2005.

Co-pending commonly assigned. U.S. Appl. No. 11/557,225, filed Nov. 7, 2006, now published as 2007-0072936A1, on Mar. 29, 2007.

Co-pending commonly assigned. U.S. Appl. No. 11/572,748, filed Aug. 22, 2005, now published as 2007-0207987A1, on Sep. 6, 2007.

* cited by examiner

FIGURE I
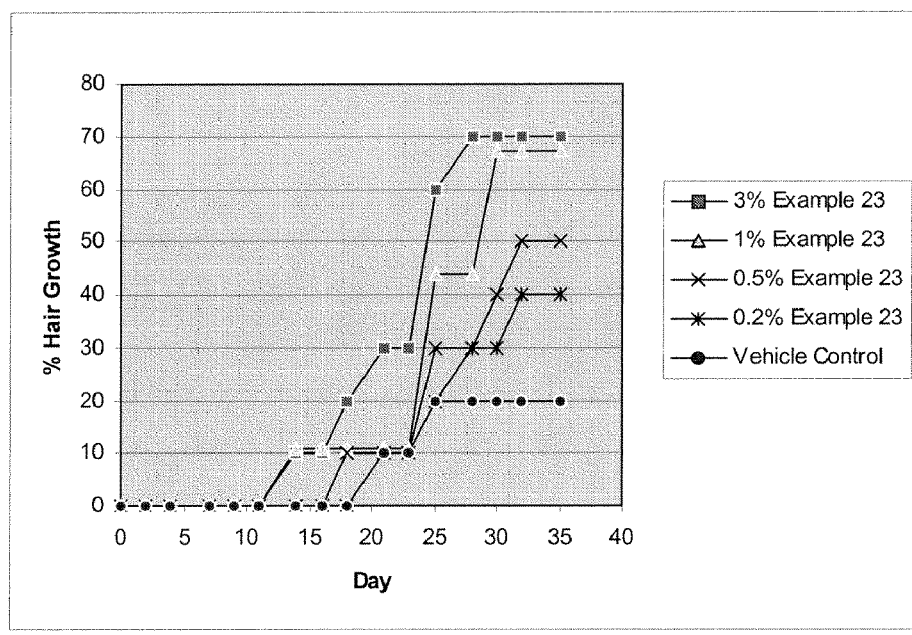

ANDROGEN RECEPTOR MODULATORS

CROSS REFERENCE TO RELATED APPLICATION

This application claims priority to U.S. Provisional Applications Ser. No's. 60/544,738, filed Feb. 13, 2004 and 60/605,647 filed Aug. 30, 2004, the contents of each are hereby incorporated by reference.

FIELD OF THE INVENTION

The present invention is directed to a new class of benzonitriles and to their use as androgen receptor modulators. Other aspects of the invention are directed to the topical use of these compounds to alleviate alopecia and oily skin.

BACKGROUND OF THE INVENTION

Alopecia, or balding, is a common problem which medical science has yet to cure. The physiological mechanism by which this hair loss occurs is not known. However, it is known that hair growth is altered in individuals afflicted with alopecia.

Hair follicles undergo cycles of activity involving periods of growth, rest, and shedding. The human scalp typically contains from 100,000 to 350,000 hair fibers or shafts, which undergo metamorphosis in three distinct stages:

(a) during the growth phase (anagen) the follicle (i.e., the hair root) penetrates deep into the dermis with the cells of the follicle dividing rapidly and differentiating in the process of synthesizing keratin, the predominant component of hair. In non-balding humans, this growth phase lasts from one to five years;
(b) the transitional phase (catagen) is marked by the cessation of mitosis and lasts from two to several weeks, and;
(c) the resting phase (telogen) in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio can be reduced to as low as 2:1.

Androgenetic alopecia arises from activation of an inherited sensitivity to androgenic hormones. It is the most common type of alopecia. It affects both men (50%) and women (30%), primarily of Caucasian origin. Gradual changes in the diameter and length of the hair shaft are experienced over time and with increasing age. Terminal hair is gradually converted to short, wispy, colorless vellus hair. As a consequence, men in their 20's and women in their 30's and 40's begin to notice their hair becoming finer and shorter. In males, most of the hair loss occurs at the front and vertex of the head. Females experience a thinning over their entire scalp. As discussed above, the anagen to telogen ratio is reduced significantly, resulting in less hair growth.

Minoxidil, a potassium channel opener, promotes hair growth. Minoxidil is available commercially in the United States under the trademark ROGAINE®. While the exact mechanism of action of minoxidil is unknown, its impact on the hair growth cycle is well documented. Minoxidil promotes the growth of the hair follicle and increases the period of time that the hair follicle is in the anagen phase (i.e. increases the anagen to telogen ratio).

While minoxidil promotes hair growth, the cosmetic efficacy of this growth can vary widely. For example, Roenigk reported the results of a clinical trial involving 83 males who used a topical solution of 3% minoxidil for a period of 19 months. Hair growth occurred in 55% of the subjects. However, only 20% of the subjects considered the growth to be cosmetically relevant. (*Clin. Res.*, 33, No. 4, 914A, 1985). Tosti reported cosmetically acceptable re-growth in 18.1% of his subjects. (*Dermatologica*, 173, No. 3, 136-138, 1986). Thus, the need exists in the art for compounds having the ability produce higher rates of cosmetically acceptable hair growth in patients with alopecia.

SUMMARY OF THE INVENTION

In accordance with the present invention, a new class of 4-oxo-benzonitriles has been discovered. These compounds, and their pharmaceutically acceptable salts, hydrates, and prodrugs thereof, may be represented by the following formula:

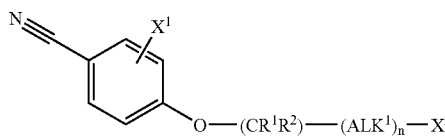

in which:
$X^1$ is represented by halogen or haloalkyl;
$X^2$ is represented by —$CR^3R^4R^5$, —CH=$CH_2$, or —C≡CH;
$R^1$ and $R^2$, are each independently represented by a substituent selected from the group consisting of hydrogen, halogen, $C_{1-6}$ alkyl, haloalkyl, hydroxyalkyl, thiol, and thioalkyl;
$R^3$, $R^4$, and $R^5$ are each independently represented by a substituent selected from the group consisting of hydrogen, halogen, $C_{1-6}$ alkyl, haloalkyl, hydroxy, hydroxyalkyl, thiol, thioalkyl and —$NR^6R^7$;
n is represented by the integer 0 or 1;
$ALK^1$ is represented by a $C_{1-8}$ linear alkylene group, in which up to 8 hydrogen atoms of the alkylene group may optionally be replaced by a substituent selected from the group consisting of $C_{1-6}$ alkyl, haloalkyl, halogen, hydroxy, hydroxyalkyl, thiol, thioalkyl, and —$NR^6R^7$;
$R^6$ and $R^7$ are each independently represented by hydrogen or $C_{1-6}$ alkyl with the proviso that:
1) if n is 0 and $X^2$ is represented by —CH=$CH_2$ or —C≡CH, then at least one of $R^1$ or $R^2$ is represented by thiol, hydroxyalkyl, or thioalkyl;
2) if n is 1 and $X^2$ is represented by —CH=$CH_2$ or —C≡CH, then in the alternative, at least one of $R^1$ or $R^2$ is represented by a substituent selected from the group consisting of thiol, hydroxyalkyl, and thioalkyl, or at least one hydrogen atom from $Alk^1$ is replaced by a substituent selected from the group consisting of hydroxy, thiol, hydroxyalkyl, and thioalkyl;
3) if n is 0 and $X^2$ is represented by —$CR^3R^4R^5$, then, in the alternative, at least one of $R^1$ or $R^2$ is represented by a substituent selected from the group consisting of thiol, hydroxyalkyl, and thioalkyl, or at least one of $R^3$, $R^4$, or $R^5$ is represented by hydroxy, hydroxyalkyl, thiol, or thioalkyl;
4) if n is 1 and $X^2$ is represented by —$CR^3R^4R^5$, then alternatively: a) at least one of $R^1$ or $R^2$ is represented by a substituent selected from the group consisting of thiol, hydroxyalkyl, and thioalkyl, b) at least one of $R^3$, $R^4$, or $R^5$ is represented by a substituent selected from the group consisting of hydroxy, hydroxyalkyl, thiol, and thioalkyl, or c) at least one hydrogen atom of $Alk^1$ is replaced with a substituent selected from the group consisting of hydroxy, thiol, thioalkyl, and hydroxyalkyl.

The compounds of Formula I are androgen receptor modulators. The compounds have affinity for the androgen receptor and will cause a biological effect by binding to the receptor. Typically, the compounds will act as antagonists. In selected embodiments they will act as partial agonists, full agonists, or tissue selective agonists. As androgen receptor modulators, the compounds can be used to treat, or alleviate, conditions associated with inappropriate activation of the androgen receptor. Examples of such conditions for antagonists include, but are not limited to, acne, excess sebum secretion, androgenic alopecia, hormone dependant cancers such as prostrate cancer, and hirsutism. Those compounds which are partial agonists, full agonists, or tissue selective agonists can be used to treat osteoporosis, hypogonadism, anemia, or to stimulate increases in muscle mass, especially in wasting diseases.

The invention is also directed to pharmaceutical compositions containing at least one of the compounds of Formula I, in an amount effective to modulate activation of the androgen receptor. In a further embodiment, the invention is directed to an article of manufacture containing a compound of Formula I, packaged for retail distribution, in association with instructions advising the consumer on how to use the compound to alleviate a condition associated with inappropriate activation of the androgen receptor. An additional embodiment is directed to the use of a compound of Formula I as a diagnostic agent to detect inappropriate activation of the androgen receptor.

In a further embodiment, the compounds of Formula I are used topically to induce and/or stimulate hair growth and/or to slow down hair loss. The compounds may also be used topically in the treatment of excess sebum and/or of acne.

BRIEF DESCRIPTION OF THE DRAWINGS

FIG. 1 illustrates the hair growth observed in a grouop of test animals.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.
b. "$C_1$-$C_6$ alkyl" refers to a branched or straight chained alkyl group containing from 1 to 6 carbon atoms, such as methyl, ethyl, n-propyl, isopropyl, n-butyl, isobutyl, pentyl, hexyl, etc.
c. "haloalkyl" refers to a branched or straight chained alkyl group containing from 1 to 6 carbon atoms, in which at least one hydrogen atom is replaced with a halogen (i.e. $C_1$-$C_6$ haloalkyl). Examples of suitable haloalkyl's include chloromethyl, difluoromethyl, trifluoromethyl, 1-fluro-2-chloro-ethyl, 5-fluoro-hexyl, 3-difluro-isopropyl, 3-chloro-isobutyl, etc.
d. "hydroxyalkyl" refers to a branched or straight chained alkyl group containing from 1 to 6 carbon atoms in which at least one hydrogen atom is replaced with a hydroxy function (i.e. $C_1$-$C_6$ hydroxyalkyl). Examples of suitable hydroxyalkyl's include hydroxymethyl, 1,2-dihydroxy-propyl, 1-hydroxy-pentyl, 6-hydroxy-hexyl, 2-hydroxy-ethyl, etc.
e. "thioalkyl" refers to a branched or straight chained alkyl group containing from 1 to 6 carbon atoms in which at least one hydrogen atom is replaced with a sulfhydryl groupl (i.e. —SH).

Examples of suitable thioalkyl's include methyl mercaptan, 2-thiol-ethyl, 1,3-dithiol-propyl, 6-thiol-hexyl, 4-thiol-pentyl, etc.

f. "linear alkylene group containing from 1 to 8 carbon atoms" refers to an alky group containing from 1 to 8 carbon atoms serving as a linking group within the molecule (i.e. no terminal —$CH_3$ function). Examples of such alkyl groups include —$CH_2$—, —$CH_2$—$(CH_2)_4$—$CH_2$—, —$CH_2$—$(CH_2)_6$—$CH_2$—, —$CH_2$—$CH_2$—$CH_2$—, —$CH_2$—$(CH_2)_2$—$CH_2$—, etc.
g. "solvate" is a crystalline form of a compound or salt thereof, containing one or more molecules of solvent of crystallization, i.e., a compound of Formula I or a salt thereof, containing solvent combined in the molecular form. A "hydrate" is a solvate in which the solvent is water.
h. "polymorph" is a compound or salt thereof, such as the compound of Formula I or a salt thereof, which occurs in at least one crystalline form.
i. "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.
j. "pharmaceutically acceptable salts" is intended to refer to either pharmaceutically acceptable acid addition salts" or "pharmaceutically acceptable basic addition salts" depending upon actual structure of the compound.
k. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents.
l. "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

m. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

n. "compound of Formula I", "compounds of the invention", and "compounds" are used interchangeably throughout the application and should be treated as synonyms.

o. "patient" refers to warm blooded animals such as, for example, guinea pigs, mice, rats, gerbils, cats, rabbits, dogs, monkeys, chimpanzees, stump tail macques, and humans.

p. "treat" refers to the ability of the compounds to either relieve, alleviate, or slow the progression of the patient's disease (or condition) or any tissue damage associated with the disease.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. A compound can also exist in different polymorphic forms and the claims should be construed as covering all such forms.

All of the compounds of Formula I contain a phenyl ring. To further exemplify the invention, the numbering system for this ring and its substitution pattern is shown below:

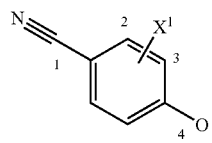

Position 1 of this phenyl ring will always be substituted with a cyano moiety as depicted above. Position 4 will be substituted with an oxygen atom forming an ether moiety. The phenyl ring will be further substituted, as depicted by $X^1$, at position 2 or 3 with a halogen atom or a haloalkyl moiety. Typically, this halogen or haloalkyl moiety will be at the 2-position. More typically it will be trifluoroalkyl, located at the 2-position of the phenyl ring.

As noted above, position 4 of the phenyl ring is substituted with an ether moiety, which will always include: $—(CR^1R^2)$-$(ALK^1)_n$—$X^2$. $AlK^1$, when present, represents a $C_1$ to $C_8$ linear alkylene moiety, such as methylene, ethylene, propylene, butylene, pentylene, hexylene, heptylene, or octylene. Up to 8 hydrogen atoms of this alkylene moiety may be replaced with one of the substituents defined above. Any single carbon atom of $Alk^1$ may be unsubstituted, monosubstituted, or disubstituted. These carbon atoms may be substituted with the same substituent or differing substituents.

The ether moiety $—(CR^1R^2)$-$(ALK^1)_n$—$X^2$ will be substituted with at least one hydroxy, thiol, hydroxyalkyl, or thioalkyl moiety. This may be accomplished by one of two alternative substitution patterns (depending upon the presence, or absence of $Alk^1$). If $Alk^1$ is not present in the molecule (i.e. n is 0), then one of, $R^3$, $R^4$, or $R^5$ may be represented by hydroxy, hydroxyalkyl, thiol, or thioalkyl, or one of $R^1$ or $R^2$ may be represented by hydroxyalkyl, thiol, or thioalkyl, If $Alk^1$ is present (i.e. n is 1), then alternatively: a) one of $R^3$; $R^4$, or $R^5$ may be represented by hydroxy, hydroxyalkyl, thiol, or thioalkyl, b) one of $R^1$ or $R^2$ may be represented by hydroxyalkyl, thiol, or thioalkyl, or c), one of the carbon atoms of $Alk^1$ may be substituted with hydroxy, hydroxyalkyl, thiol, or thioalkyl.

This requirement that the molecule contain a hydroxy or thiol function should not be construed as limiting the molecule to only one hydroxy or thiol moiety. If desired, the ether moiety $—(CR^1R^2)$-$(ALK^1)_n$—$X^2$ may contain multiple hydroxy, hydroxyalkyl, thioalkyl and thiol functions consistent with the substitution pattern described above.

In a further optional embodiment of the invention, for those compounds in which $X^2$ is $CR^3R^4R^5$ and n is 0; at least one of $R^1$, $R^2$, $R^3$, $R^4$, or $R^5$ is represented by $C_1$-$C_6$ alkyl, haloalkyl, thioalkyl, or hydroxyalkyl (i.e. the ether residue, $—CR^1R^2$-$(Alk^1)_n$—$X^2$, is branched alky). In an additional optional embodiment, for those compound in which $X^2$ is $CR^3R^4R^5$ and n is 1; at least one of $R^1$, $R^2$, $R^3$, $R^4$, or $R^5$ is represented by $C_1$-$C_6$ alkyl, haloalkyl, thioalkyl, or hydroxyalkyl or alternatively one hydrogen atom of $Alk^1$ is replaced with a substituent selected from the group consisting of $C_1$-$C_6$ alkyl, haloalkyl, thioalkyl, or hydroxyalkyl (i.e. the ether residue, $—CR^1R^2$-$(Alk^1)_n$—$X^2$, is branched alky).

More specific embodiments of the invention are directed to compounds of Formula I in which:

1) $X^1$ is $CF_3$ and is located at the 2-position of the phenyl ring and $X^2$ is $CR^3R^4R^5$, in which one of $R^3$, $R^4$, or $R^5$ is hydroxy;
2) $X^1$ is Cl and is located at the 2-position of the phenyl ring and $X^2$ is $CR^3R^4R^5$, in which one of $R^3$, $R^4$, or $R^5$ is hydroxy;
3) $X^1$ is $CF_3$ and is located at the 2-position of the phenyl ring, $R^1$ is hydrogen and $R^2$ is $C_1$-$C_6$ alkyl, n is 1 in which $Alk^1$ is methylene, ethylene, propylene, or butylenes, $X^2$ is $—CR^3R^4R^5$, in which $R^3$ is hydrogen or $C_1$-$C_6$ alkyl, $R^4$ is hydrogen or $C_1$-$C_6$ alkyl, and $R^5$ is hydroxy;
4) $X^1$ is $CF_3$ and is located at the 2-position of the phenyl ring, $R^1$ is hydrogen or $C_1$-$C_6$ alkyl, $R^2$ is hydrogen, n is 0, and $x^2$ is $CR^3R^4R^5$, in which $R^3$ is hydroxy or hydroxylalkyl, $R^4$ is hydrogen or $C_1$-$C_6$ alkyl and $R^5$ is hydrogen; or
5) $X^1$ is $CF_3$ or Cl, and is located at the 2-position of the phenyl ring, $R^1$ and $R^2$ are each hydrogen, n is 1 in which $Alk^1$ is methylene, ethylene, propylene, or butylene, which is substituted with 1 to 3 substituents independently selected from hydroxy, hydroxyalkyl or $C_1$-$C_6$ alkyl and $X^2$ is $CR^3R^4R^5$, in which $R^3$ is hydrogen or hydroxy, and $R^4$ and $R^5$ are each hydrogen or $C_1$-C6 alkyl.

More specific examples of compounds encompassed by Formula I include:

i) 4-(2-hydroxy-1-ethyl-propoxy)-2-trifluoromethyl-benzonitrile;
ii) 4-(2-hydroxy-1-methyl-propoxy)-2-trifluoromethyl-benzonitrile;
iii) 4-(3-hydroxy-1-methyl-butoxy)-2-trifluoromethyl-benzonitrile;
iv) 4-(2-hydroxy-6-methyl-heptyloxy)-2-trifluoromethyl-benzonitrile;
v) 4-(2-hydroxy-7-hydroxy-heptyloxy)-2-trifluoromethyl-benzonitrile;
vi) 4-(2-hydroxy-octyloxy)-2-trifluoromethyl-benzonitrile;
vii) 4-(2-hydroxy-8-hydroxy-8methyl-octyloxy)-2-trifluoromethyl-benzonitrile;
viii) 4-(2-hydroxy-oct-7-enyloxy)-2-trifluoromethyl-benzonitrile;
ix) 4-(2-hydroxy-oct-7-ynyloxy)-2-trifluoromethyl-benzonitrile;
x) 4-(2-ethyl-3-Hydroxy-butoxy)-2-trifluoromethyl-benzonitrile;
xi) 4-(3-hydroxy-butoxy)-2-trifluoromethyl-benzonitrile;
xii) 4-(3-hydroxy-hex-5-enyloxy)-2-trifluoromethyl-benzonitrile;
xiii) 4-(3-hydroxy-hex-5-ynyloxy)-2-trifluoromethyl-benzonitrile;
xiv) 4-(3-hydroxy-2-methyl-butoxy)-2-trifluoromethyl-benzonitrile;
xv) 4-(3-hydroxy-2-propyl-butoxy)-2-trifluoromethyl-benzonitrile;
xvi) 4-(3-hydroxy-2, 2-dimethyl-propoxy)-2-trifluoromethyl-benzonitrile;
xvii) 4-(3-hydroxy-3-methyl-butoxy)-2-trifluoromethyl-benzonitrile;
xviii) 4-(4-hydroxy-3-methyl-pentoxy)-2-trifluoromethyl-benzonitrile;
xix) 4-(3-hydroxy-2,2,4-trimethyl-pentyloxy)-2-trifluoromethyl-benzonitrile;
xx) 4-(2-ethyl-3-Hydroxy-hexyloxy)-2-trifluoromethyl-benzonitrile;
xxi) 4-[2-(1-hydroxy-ethyl)-hexyloxy]-2-trifluoromethyl-benzonitrile;
xxii) 4-(3-hydroxy-1-methyl-butoxy)-2-trifluoromethyl-benzonitrile;
xxiii) 4-(3-hydroxy-1-methyl-2-ethyl-butoxy)-2-trifluoromethyl-benzonitrile
xxiv) 4-(4-hydroxy-butoxy)-2-trifluoromethyl-benzonitrile;
xxv) 4-(6-hydroxy-heptoxy)-2-trifluoromethyl-benzonitrile;
xxvi) 4-(4-Hydroxy-heptyloxy)-2-trifluoromethyl-benzonitrile;
xxvii) 4-(4-hydroxy-1-propyl-butoxy)-2-trifluoromethyl-benzonitrile;
xxviii) 4-(4-hydroxy-1-methyl-pentyloxy)-2-trifluoromethyl-benzonitrile;
xxix) 4-(5-hydroxy-pentyloxy)-2-trifluoromethyl-benzonitrile;
xxx) 4-(5-hydroxy-hexyloxy)-2-trifluoromethyl-benzonitrile;
xxxi) 4-(5-hydroxy-3-methyl-pentyloxy)-2-trifluoromethyl-benzonitrile;
xxxii) 2-chloro-4-(3-hydroxy-2,2,4-trimethyl-pentyloxy)-benzonitrile;
xxxiii) 2-chloro-4-(4-hydroxy-butoxy)-benzonitrile;
xxxiv) 2-chloro-4-(3-hydroxy-propoxy)-benzonitrile;
xxxv) 2-chloro-4-(1-hydroxymethyl-allyloxy)-benzonitrile;
xxxvi) 2-chloro-4-(1-hydroxymethyl-acetyleneloxy)-benzonitrile;
xxxvii) 2-chloro-4-(3-hydroxy-2-methyl-propoxy)-benzonitrile;
xxxviii) 2-chloro-4-(5-hydroxy-pentyloxy)-benzonitrile;
xxxix) 2-chloro-4-(4-hydroxy-1-methyl-pentyloxy)-benzonitrile, or;
xl) 2-chloro-4-(5-hydroxy-3-methyl-pentyloxy)-benzonitrile.

Synthesis

The compounds of Formula I can be prepared using methods analogous to those known in the art for the preparation of ethers. The reader's attention is directed to European Patent Application Number 58932, published Sep. 1, 1982, the contents of which are hereby incorporated by reference for a description of such reactions. Scheme I below provides an overview of one such technique:

SCHEME I

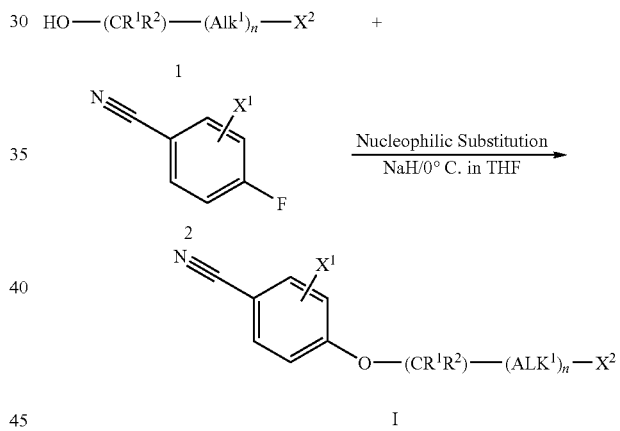

As depicted above, one of the starting materials is an alcohol as depicted by structure 1. $R^1$, $R^2$, $Alk^1$ and $X^2$ should be represented by the same substituent as is desired in the final product. These alcohols are known in the art and may be purchased from known commercial sources. Alternatively, they can be prepared as described in Tetrahedron: Asymmetry, 1991 Vol. 2, page 569.

The other starting material is a 4-fluoro-benzonitrile as depicted by structure 2. $X^1$ should be represented by the same substituent as desired in the final product. These benzonitriles are known in the art and may be synthesized as described by Japanese Patent Application Number 01097937.

The nucleophilic substitution depicted above may be carried out as is known in the art. The alcohol of structure 1 is contacted with a slight excess of a base, such as sodium hydride, to produce an alkoxide ion. The reaction is carried out in an aprotic solvent, such as tetrahydrofuran, under an inert atmosphere (typically nitrogen) at a temperature of about 0° C. The alcohol is stirred with the base for a period of time ranging from 5 to 60 minutes.

One equivalent of the 4-fluoro-benzonitrile of structure 2 is then added to the reaction medium and the reactants are stirred for a sufficient period of time to allow the alkoxide ion to displace the fluorine from the benzonitrile. This typically takes from 30 minutes to 24 hours. The reaction e is typically allowed to warm to room temperature.

The desired product of Formula I can be recovered by extraction, evaporation, or other techniques known in the art. It may then be optionally purified by chromatography, recrystallization, distillation, or other techniques known in the art.

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, *Protective Groups in Organic Synthesis*, John Wiley & Sons, New York, 1991.

Some of the compounds of this invention are acidic and they form salts with a pharmaceutically acceptable cation. Some of the compounds of this invention are basic and form salts with pharmaceutically acceptable anions. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

Medical and Cosmetic Uses

The compounds of Formula I are androgen receptor modulators. They can be used to alleviate conditions associated with inappropriate activation of the androgen receptor. Compounds acting as androgen antagonists may be used to treat, or alleviate, hormone dependent cancers such as prostate carcinomas, benign hyperplasia of the prostate, acne, hirsutism, excess sebum, alopecia, hypertrichosis, precocious puberty, prostamegaly, virilization, and polycystic ovary syndrome. Compounds acting as partial agonists, or full agonists, may be used to treat, or alleviate, male hypogonadism, male sexual dysfunction (impotence, male dysspemtatogenic sterility), abnormal sex differentiation (male hermaphroditism), male delayed puberty, male infertility, aplastic anemia, hemolytic anemia, sickle cell anemia, idiopathic thrombocytopenic purpura, myelofibrosis, renal anemia, wasting diseases (post operative, malignant tumor, trauma, chronic renal disease, burn or AIDS induced), abatement of pain in terminal carcinoma of female genitalia, inoperable breast cancer, mastopathy, endometriosis, female sexual dysfunction, osteoporosis, wound healing and muscle tissue repair.

In order to exhibit the therapeutic properties described above, the compounds need to be administered in a quantity sufficient to modulate activation of the androgen receptor. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally), rectally, or topically.

In a typical embodiment, the compounds are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. The dermatological preparation will be applied to the affected area from 1 to 4 times daily. "Dermatologically acceptable" refers to a carrier which may be applied to the skin or hair, and which will allow the drug to diffuse to the site of action. More specifically, it refers the site where inhibition of activation of an androgen receptor is desired.

In a further embodiment, the compounds are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. Androgenic alopecia is also common in women where it usually present as a diffuse hair loss rather than showing the patterning seen in men.

While the compounds will most typically be used to alleviate androgenic alopecia, the invention is not limited to this specific condition. The compounds may be used to alleviate any type of alopecia. Examples of non-androgenic alopecia include alopecia areata, alopecia due to radiotherapy or chemotherapy, scarring alopecia, stress related alopecia, etc. As used in this application, "alopecia" refers to partial or complete hair loss on the scalp.

Thus, the compounds can be applied topically to the scalp and hair to prevent, or alleviate balding. Further, the compound can be applied topically in order to induce or promote the growth of hair on the scalp.

In a further embodiment of the invention, a compound of Formula I is applied topically in order to prevent the growth of hair in areas where such hair growth is not desired. One such use will be to alleviate hirsutism. Hirsutism is excessive hair growth in areas that typically do not have hair (i.e. a female face). Such inappropriate hair growth occurs most commonly in women and is frequently seen at menopause. The topical administration of the compounds will alleviate this condition leading to a reduction, or elimination of this inappropriate, or undesired, hair growth.

The compounds may also be used topically to decrease sebum production and more specifically to alleviate oily skin. Likewise the compounds can be used topically to alleviate acne.

In a further embodiment, those compounds acting as partial agonists, or full agonists, may be used to treat, or alleviate, osteoporosis. Osteoporosis is characterized by bone loss, resulting from an imbalance between bone resorption (destruction) and bone formation, which starts in the fourth decade and continues throughout life at the rate of about 1-4% per year (Eastell, Treatment of postmenopausal osteoporosis, New Eng. J. Med. 338: 736, 1998). In the United States, there are currently about 20 million people with detectable fractures of the vertebrae due to osteoporosis. In addition, there are about 250,000 hip fractures per year due to osteoporosis, associated with a 12%-20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs) and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site; higher in the trabecular bone of the vertebrae than in the cortex of the long bones, the bone resorption inhibitors are less effective in increasing hip BMD and preventing hip fracture. Therefore, osteoanabolic agents, which increase cortical/periosteal bone formation and bone mass of long bones, would address an unmet need in the treatment of osteoporosis especially for patients with high risk of hip fractures.

A number of studies demonstrate that androgens are osteoanabolic in women and men. Anabolic steroids, such as nandrolone decanoate or stanozolol, have been shown to increase bone mass in postmenopausal women. Beneficial effects of androgens on bone in post- menopausal osteoporosis are well documented in recent studies using combined testosterone and estrogen administration (Hofbauer, et al., Androgen effects on bone metabolism: recent progress and controversies, Eur. J. Endocrinol. 140, 271-286, 1999). Thus those compounds of Formula I exhibiting agonist or partial agonist activity may be used to treat, or alleviate, osteoporosis, including primary osteoporosis such as senile, postmenopausal and juvenile osteoporosis, as well as secondary osteoporosis, such as osteoporosis due to hyperthyroidism or Cushing syndrome (due to corticosteroid treatment), acromegaly, hypogonadism, dysosteogenesis and hypophosphatasemia. Other bone related indications amendable to treat from androgen agonists include osteoporotic fracture, childhood idiopathic bone loss, alveolar bone loss, mandibular bone loss, bone fracture, osteotomy, periodontitis, or prosthetic ingrowth.

Those compounds acting as agonists, or partial agonists, can also be used to stimulate muscle mass in patients afflicted with wasting diseases, such as AIDS, cancer cachexia, burns, renal disease, etc. Patients suffering from trauma, bedsores, age, etc. can also benefits from the anabolic effects of androgens.

Co-Administration

In a further embodiment of the invention, the compounds of Formula I can be co-administered with other compounds to further enhance their activity, or to minimize potential side effects. For example, potassium channel openers, such as minoxidil, are known to stimulate hair growth and to induce anagen. Examples of other potassium channel openers include (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran, diaxozide, and PO 1075 which is under development by Leo Pharmaceuticals Thyroid hormone is also known to stimulate hair growth. Synthetic thyroid hormone replacements (i.e. thyromimetics) have also been shown to stimulate hair growth. Such thyromimetics have been described in the literature previously. The reader's attention is directed to European Patent Application No. 1262177, the contents of which are hereby incorporated by reference, for a discussion of such compounds and their use to alleviate alopecia. One particular compound of interest is 2-{4-[3-(4-Fluoro-benzyl)-4-hydroxy-phenoxy]-3,5-dimethyl-phenyl}-2H -[1,2,4]triazine-3,5-dione. Anti-androgens can work by a number of different mechanisms. For example, some compounds block the conversion of testosterone to 5-α-dihydrotestosterone, which is responsible for the biological effect in many tissues. 5-Alpha-reductase inhibitors, such as finasteride, have been shown to stimulate hair growth. Finasteride is commercially available from Merck under the trade name Propecia®. Examples of other 5-α-reductase inhibitors include dutasteride (Glaxo Smithkline). Such compounds can be co-administered with the compounds of Formula I to alleviate alopecia.

Protein kinase C inhibitors have also been shown to stimulate hair growth and induce anagen. Calphostin C, which is a selective inhibitor of protein kinase C, has been shown to induce anagen. Other selective protein kinase C inhibitors, such as hexadecylphosphocholine, palmitoyl-DL-carnitine chloride, and polymyxin B sulfate have also been shown to induce anagen. Skin Pharmacol Appl Skin Physiol 2000 May-August; 13(3-4):133-42 Any such protein kinase C inhibitor can be co-administered with a compound of Formula I to alleviate alopecia.

Immunophilins are a family of cytoplasmic proteins. Their ligands include cyclosporin, FK506, and rapamycin. They are derived from fungi and were developed primarily for their potent immunosuppressive properties. Cyclosporin binds to the protein, cyclophilin, while FK506 and rapamycin bind to FK binding protein (FKBP). All of these compounds have been shown to stimulate hair growth and induce anagen. Any such immunophilin ligands can be co-administered with a compound of Formula I to alleviate alopecia.

As used in this application, co-administered refers to administering a compound of Formula I with a second anti-alopecia agent, typically having a differing mechanism of action, using a dosing regimen that promotes hair growth in the patient. This can refer to simultaneous dosing, dosing at different times during a single day, or even dosing on different days. The compounds can be administered separately or can be combined into a single formulation. Techniques for preparing such formulations are described below.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair.

Pharmaceutical and cosmetic compositions can be manufactured utilizing techniques known in the art. Typically an effective amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Reminqton's Pharmaceutical Science*, Edition 17, Mack Publishing Co., Easton, Pa. for a discussion of how to prepare such formulations.

The compositions according to the invention can also consist of solid preparations constituting cleansing soaps or bars. These compositions are prepared according to the usual methods.

The compounds can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of the invention will typically be packaged for retail distribution (i.e. an article of manufacture). Such articles will be labeled and packaged in a manner to instruct the patient how to use the product. Such instructions will include the condition to be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data is being presented in order to further illustrate the invention. This disclosure should not be construed as limiting the invention in any manner.

EXAMPLE 1

(1S,2S)-4-(2-Hydroxy-1-methyl-propoxy)-2-trifluoromethyl-benzonitrile

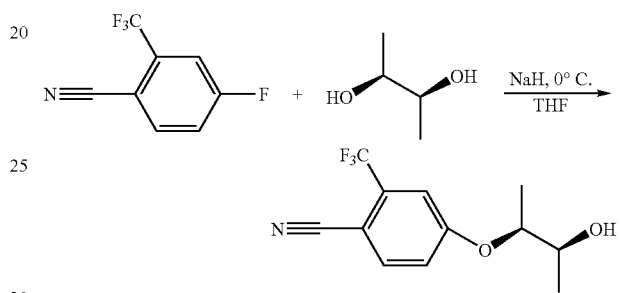

NaH (0.20 g, 4.14 mmol) was suspended in 15 ml of dry THF, then (2S,3S)-(+)-2,3-butanediol was added (0.32 g, 3.45 mmol, in 5 ml of dry THF). This mixture was stirred at 0° C. for 10 minutes, followed by the addition of 4-fluoro-2-trifluoromethyl-benzonitrile. The reaction mixture was stirred, 0° C. for 1 hour, under a nitrogen atmosphere. The mixture was then stirred for an additional 2 hours, at room temperature, in a hood. The reaction was quenched with 25 ml of distilled water, extracted with ethyl acetate (3×20 ml). The product was purified by column chromatography, using hexane: ethyl acetate=5:1 to 1:1 as elute to yield the pure product.

MS: 260.0 (M+1 for $C_{12}H_{12}F_3NO_2$). LCMS: C-18 Column (50% $H_2O$/50% $CH_3CN$), Ret. Time: 1.81 min

EXAMPLES 2-27

Using the general procedure of Example 1, but substituting the relevant starting materials, the compounds described in Table I were prepared. Chromatography was performed on a Foxy 200 fraction collector, using prepared Biotage Silicon Gel column, (water:methylnitrile was used as the elute solvent, 50:50, in all examples except 8, 16, 17, 26 which utilized a 25:75 admixture of water:methylnitrile). The mass spectra in Table I were recorded with an Hewlett Packard mass spectrometer.

TABLE 1

| Example | Structure | Name | RT | Base Peak |
| --- | --- | --- | --- | --- |
| 2 | 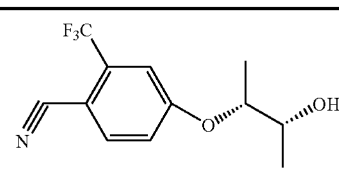 | (1R,2R)-4-(2-Hydroxy-1-methyl-propoxy)-2-trifluoromethyl-benzonitrile | 1.85 | MS: 260.0 (M + 1 for $C_{12}H_{12}F_3NO_2$) |

TABLE 1-continued

| Example | Structure | Name | RT | Base Peak |
|---|---|---|---|---|
| 3 | 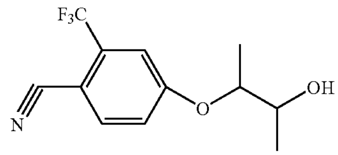 | 4-(2-Hydroxy-1-methyl-propoxy)-2-trifluoromethyl-benzonitrile | 1.80 | MS: 260.0 (M + 1 for $C_{12}H_{12}F_3NO_2$) |
| 4 | 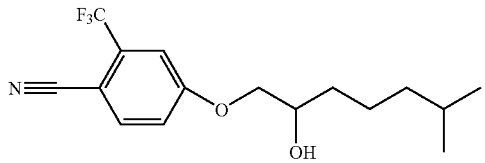 | 4-(2-Hydroxy-6-methyl-heptyloxy)-2-trifluoromethyl-benzonitrile | 1.95 | MS: 316.2 (M + 1 for $C_{16}H_{20}F_3NO_2$) |
| 5 | 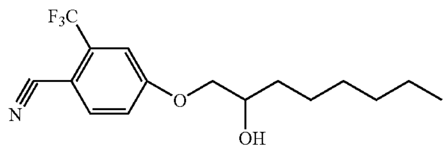 | 4-(2-Hydroxy-octyloxy)-2-trifluoromethyl-benzonitrile | 1.76 | MS: 316.2 (M + 1 for $C_{16}H_{20}F_3NO_2$) |
| 7 | 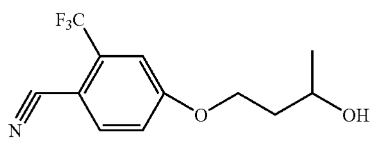 | 4-(3-Hydroxy-butoxy)-2-trifluoromethyl-benzonitrile | 2.50 | MS: 260.1 (M + 1 for $C_{12}H_{12}F_3NO_2$) |
| 8 | 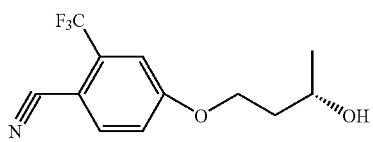 | (3S)-4-(3-Hydroxy-butoxy)-2-trifluoromethyl-benzonitrile | 0.91 | MS: 260.1 (M + 1 for $C_{12}H_{12}F_3NO_2$) |
| 9 | 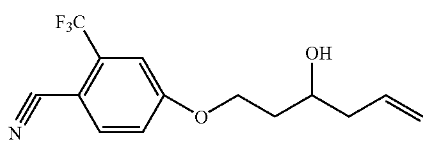 | 4-(3-Hydroxy-hex-5-enyloxy)-2-trifluoromethyl-benzonitrile | 2.42 | MS: 280.0 (M + 1 for $C_{14}H_{14}F_3NO_2$) |
| 10 | 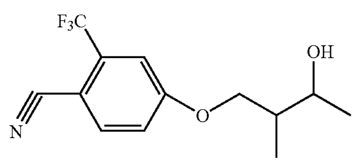 | 4-(3-Hydroxy-2-methyl-butoxy)-2-trifluoromethyl-benzonitrile | 2.12 | MS: 274.0 (M + 1 for $C_{13}H_{14}F_3NO_2$) |
| 11 | 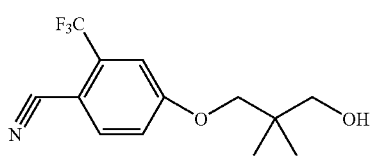 | 4-(3-Hydroxy-2,2-dimethyl-propoxy)-2-trifluoromethyl-benzonitrile | | |
| 12 | 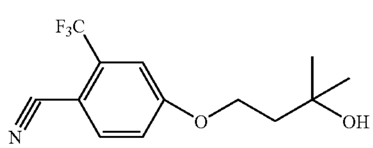 | 4-(3-Hydroxy-3-methyl-butoxy)-2-trifluoromethyl-benzonitrile | 2.25 | MS: 274.1 (M + 1 for $C_{13}H_{14}F_3NO_2$) |
| 13 | 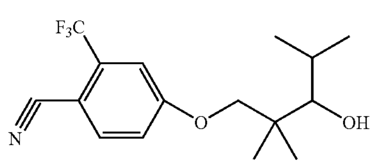 | 4-(3-Hydroxy-2,2,4-trimethyl-pentyloxy)-2-trifluoromethyl-benzonitrile | | |

TABLE 1-continued

| Example | Structure | Name | RT | Base Peak |
|---|---|---|---|---|
| 14 | 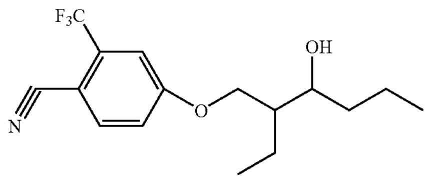 | 4-(2-Ethyl-3-Hydroxy-hexyloxy)-2-trifluoromethyl-benzonitrile | 3.8 | MS: 316.2 (M + 1 for $C_{16}H_{20}F_3NO_2$) |
| 15 | 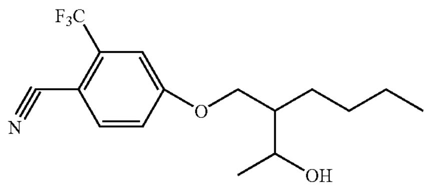 | 4-[2-(1-Hydroxy-ethyl)-hexyloxy]-2-trifluoromethyl-benzonitrile | 1.6 | MS: 316.2 (M + 1 for $C_{16}H_{20}F_3NO_2$) |
| 16 | 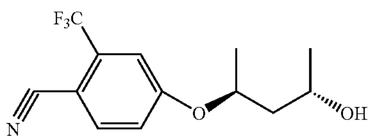 | (1S,3S)-4-(3-Hydroxy-1-methyl-butoxy)-2-trifluoromethyl-benzonitrile | 1.03 | MS: 274.0 (M + 1 for $C_{13}H_{14}F_3NO_2$) |
| 17 | 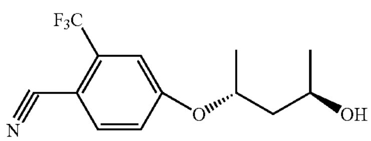 | (1R,3R)-4-(3-Hydroxy-1-methyl-butoxy)-2-trifluoromethyl-benzonitrile | 1.02 | MS: 274.0 (M + 1 for $C_{13}H_{14}F_3NO_2$) |
| 18 | 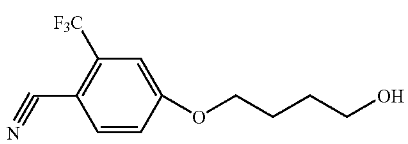 | 4-(4-Hydroxy-butoxy)-2-trifluoromethyl-benzonitrile | | MS: 260.0 (M + 1 for $C_{12}H_{12}F_3NO_2$) |
| 19 | 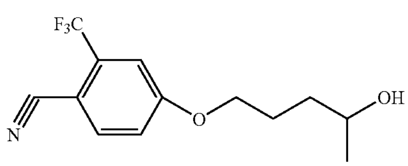 | 4-(4-Hydroxy-butoxy)-2-trifluoromethyl-benzonitrile | 1.52 | MS: 274.0 (M + 1 for $C_{13}H_{14}F_3NO_2$) |
| 20 | 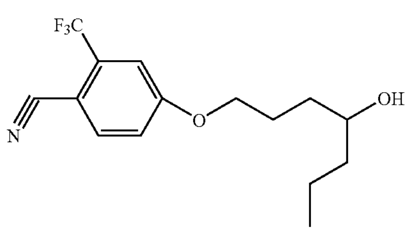 | 4-(4-Hydroxy-heptyloxy)-2-trifluoromethyl-benzontrile | 3.10 | MS: 302.1 (M + 1 for $C_{15}H_{18}F_3NO_2$) |
| 21 | 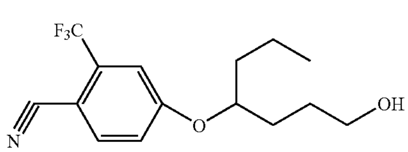 | 4-(4-Hydroxy-1-propyl-butoxy)-2-trifluoromethyl-benzonitrile | 3.16 | MS: 302.1 (M + 1 for $C_{15}H_{18}F_3NO_2$) |

TABLE 1-continued

| Example | Structure | Name | RT | Base Peak |
|---|---|---|---|---|
| 22 | 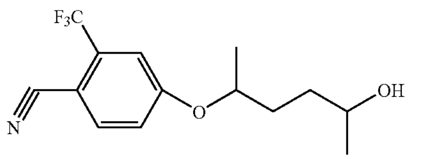 | 4-(4-Hydroxy-1-methyl-pentyloxy)-2-trifluoromethyl-benzonitrile | 2.27 | MS: 288.1 (M + 1 for $C_{14}H_{16}F_3NO_2$) |
| 23 | 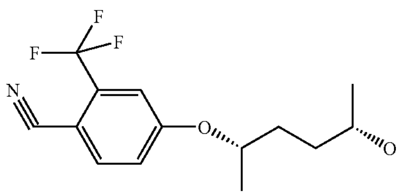 | (1S,4S)-4-(4-Hydroxy-1-methylpentyloxy)-2-trifluoromethyl-benzonitrile | 2.29 | MS: 288.1 (M + 1 for $C_{14}H_{16}F_3NO_2$ |
| 24 | 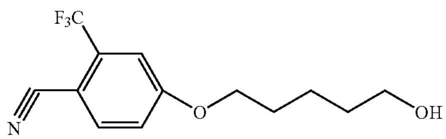 | 4-(5-Hydroxy-pentyloxy)-2-trifluoromethyl-benzonitrile | 1.94 | MS: 274.0 (M + 1 for $C_{13}H_{14}F_3NO_2$) |
| 25 | 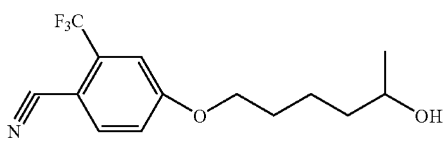 | 4-(5-Hydroxy-hexyloxy)-2-trifluoromethyl-benzonitrile | 2.31 | MS: 288.0 (M + 1 for $C_{14}H_{16}F_3NO_2$) |
| 26 | 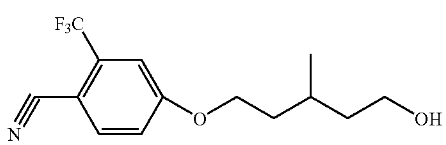 | 4-(5-Hydroxy-3-methyl-pentyloxy)-2-trifluoromethyl-benzonitrile | 1.01 | MS: 288.2 (M + 1 for $C_{14}H_{16}F_3NO_2$) |
| 27 | 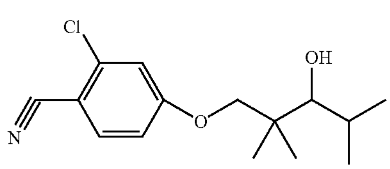 | 2-Chloro-4-(3-Hydroxy-2,2,4-trimethyl-pentyloxy)-benzonitrile | 1.70 | MS: 282.1 (M + 1 for $C_{15}H_{20}ClNO_2$) |
| 6 | 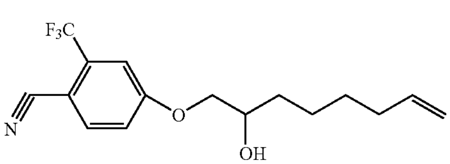 | 4-(2-Hydroxy-oct-7-enyl-oxy)-2-trifluoromethyl-benzonitrile | 3.19 | MS: 314.1 (M + 1 for $C_{16}H_{18}F_3NO_2$) |

EXAMPLE 28

2-Chloro-4-(4-hydroxy-1-methyl-pentyloxy)-benzonitrile

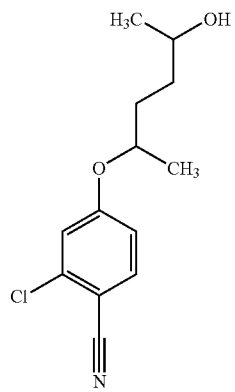

To a solution of 2,5-hexanediol (28 mg, 0.240 mmol) in tetrahydrofuran was added an excess of potassium butoxide. The admixture was stirred, briefly, and 2-chloro-4-fluoro-benzonitrile (37 mg, 0.240 mmol) was added. The admixture was stirred at room temperature for 72 hours. Purification by reverse phase high pressure chromatography eluting with a solvent gradient (15% of 0.1% formic acid/CH$_3$CN in 0.1% formic acid/water to 100% of 0.1% formic acid/water) provided 28.4 mg of 2-chloro-4-(4-hydroxy-1-methyl-pentyloxy)-benzonitrile. $^1$H NMR (CDCl$_3$) δ 7.50 (d, 1H), 6.95 (m, 1H), 6.79 (br d, 1H), 4.43 (m, 1H), 3.79 (m, 1H), 1.89-1.40 (m, 4H), 1.30 (d, 3H), 1.17 (d, 3H); MS m/z 253.

EXAMPLE 29

2-Chloro-4-(3-hydroxy-propoxy)-benzonitrile

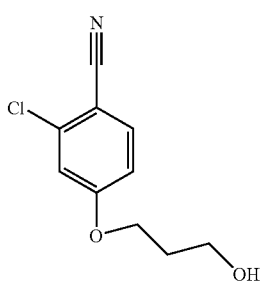

To 1,3-propanediol (320 mg, 4.2 mmol) was added sodium (21 mg, 0.92 mmol). The mixture is stirred at room temperature for 10 minutes and 2-chloro-4-fluoro-benzonitrile (156 mg, 1.0 mmol) was added. The reaction was heated to 105° C. for 24 hours. The reaction was cooled to room temperature, was diluted with water and was extracted with Et$_2$O (3×). The organic solution was dried (MgSO$_4$), filtered and concentrated. The residue was purified by reverse phase high pressure chromatography eluting with a solvent gradient (15% of 0.1% formic acid/CH$_3$CN in 0.1% formic acid/water to 100% of 0.1% formic acid/water) to provide 107 mg of 2-chloro-4-(3-hydroxy-propoxy)-benzonitrile. $^1$H NMR (CDCl$_3$) δ 7.54 (d, 1H), 7.00 (m, 1H), 6.85 (dd, 1H), 4.15 (t, 2H), 3.83 (t, 2H), 2.04 (m, 2H).

EXAMPLE 30

2-Chloro-4-(4-hydroxy-butoxy)-benzonitrile

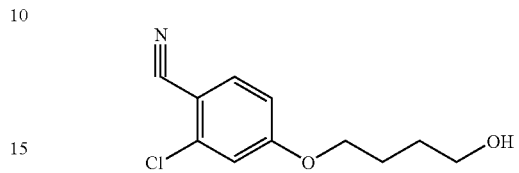

Following the procedure described for Example 29, 1,4-butanediol (1 mL, 10 mmol) was reacted with 2-chloro-4-fluoro-benzonitrile (159 mg, 1.0 mmol) for 24 hours at room temperature. Purification by reverse phase high pressure chromatography eluting with a solvent gradient (15% of 0.1% formic acid/CH$_3$CN in 0.1% formic acid/water to 100% of 0.1% formic acid/water) provided 10 mg of 2-chloro-4-(4-hydroxy-butoxy)-benzonitrile. $^1$H NMR (CDCl$_3$) δ 7.54 (d, 1H), 6.98 (d, 1H), 6.83 (dd, 1H), 4.03 (t, 2H), 3.71 (t, 2H), 1.90 (m, 2H), 1.72 (m, 2H); MS 226.1 (M+1).

EXAMPLE 31

2-Chloro-4-(1-hydroxymethyl-allyloxy)-benzonitrile

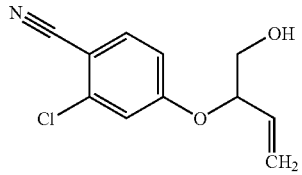

Step A: 1-(tert-Butyl-dimethyl-silanyloxy)-but-3-en-2-ol

To a solution of (+/−)-3-butene-1,2-diol (500 mg, 5.67 mmol) in CH$_2$Cl$_2$ (25 mL) was added imidazole (444 mg, 6.53 mmol). The solution was cooled to 0° C. and t-butyidimethylsilyl chloride (1.0 M in THF, 6.24 mL, 6.24 mmol) was added. The reaction was stirred at 0° C. for 15 minutes and at room temperature for 1 hour and 30 minutes. The mixture was diluted with aqueous NH$_4$Cl and extracted with CH$_2$Cl$_2$ (3×). The organic solution was washed with brine, dried (MgSO$_4$), filtered and concentrated. The residue was purified by medium pressure chromatography eluting with a solvent gradient (5% EtOAc in hexanes to 100% EtOAc) to provide 827.5 mg of 1-(tert-butyl-dimethyl-silanyloxy)-but-3-en-2-ol. $^1$H NMR (CDCl$_3$) δ 5.81 (m, 1H), 5.34 (d, 1H), 5.19 (d, 1H), 4.17 (m, 1H), 3.66 (dd, 1H), 3.45 (dd, 1H), 0.90 (s, 9H), 0.08 (s, 6H); MS m/z 202.

Step B: 4-[1-(tert-Butyl-dimethyl-silanyloxymethyl)-allyloxy]-2-chloro-benzonitrile To a solution of 1-(tert-butyl-dimethyl-silanyloxy)-but-3-en-2-ol (1.102 g, 5.45 mmol) in THF (26 mL) at −78° C. was added potassium tert-butoxide (1.0 M in THF, 5.99 mL, 5.99 mmol). The solution was stirred for 15 minutes and 2-chloro-4-fluoro-benzonitrile (847 mg, 5.45 mmol) was added at −78° C. The reaction was stirred at room temperature for 24 hours, quenched with water and extracted with EtOAc (3×). The organic solution was washed with water and brine, dried (MgSO₄), filtered and concentrated to provide 1.67 g of a 1:1 mixture of 4-[1-(tert -butyl-dimethyl-silanyloxymethyl)-allyloxy]-2-chloro-benzonitrile and 4-[2-(tert -butyl-dimethyl-silanyloxy)-but-3-enyloxy]-2-chloro-benzonitrile. $^1$H NMR (CDCl₃) δ 7.55 (m, 2H), 7.02 (m, 2H), 5.91-5.78 (m, 2H), 5.42-5.22 (m, 4H), 4.75 (m, 1H), 4.51 (m, 1H), 3.90 (m, 2H), 3.79 (m, 2H), 0.89 (s, 9H), 0.87 (s, 9H), 0.07 (s, 6H), 0.04 (s, 6H).

Step C: 2-Chloro-4-(1-hydroxymethyl-allyloxy)-benzonitrile

To a solution of the regioisomer mixture above, Example 31, Step B, (1.67 g, 4.95 mmol) in THF (15 mL) was added tert-butyl ammonium fluoride (1.0 M in THF, 5.44 mL, 5.44 mmol). The reaction was stirred at room temperature for 15 minutes, was diluted with aqueous NH₄Cl and extracted with EtOAc (3×). The organic solution was washed with brine, dried (MgSO₄), filtered and concentrated. The residue was purified by medium pressure chromatography eluting with a solvent gradient (hexanes to 100% EtOAc in hexanes over 70 minutes) to provide 112 mg of 2-chloro-4-(1-hydroxymethyl-allyloxy)-benzonitrile. $^1$H NMR (CDCl₃) δ 7.55 (d, 1H), 7.04 (d, 1H), 6.89 (dd, 1H), 5.85-5.76 (m, 1H), 5.38 (m, 2H), 4.80 (m, 1H), 3.80 (m, 2H).

EXAMPLE 31 A

This Example further illustrates the preparation of (1S,4S)-4-(4-hydroxy-1-methylpentyoxy)-2-trifluoromethyl-benzonitrile, the product of Example 23.

NaH (60% in mineral oil) was suspended in 100 ml of dry THF, it was stirred and cooled to 0° C. under N₂ for 10 min before adding the (2S,5S)-(+)-2,5-hexanediol (12.g in 120 ml of dry THF). The diol was added drop wise through a dropping funnel over 30 min., this mixture was stirred at 0° C. for 60 min, then RT 30 min., it was re-cooled to 0° C. before adding the 4-fluoro-2-(trifluoromethyl)benzonitrile (20 g in 80 ml of dry THF) over 30 min. The reaction was then stirred at 0° C. to RT under N₂ (11 am-9 am the next day). The reaction was monitored by TLC (Hex:Ethyl acetate=1:1) and LC/MS.

Purification: The crude product was dissolved in 80 ml of mixture solvent (hexane:ethyl acetate=3:1), column purification using hexane:ethyl acetate=5:1 to 1:1 as the elute to yield 22 g of the pure desired product.

EXAMPLE 32

The compounds of Formula I have affinity for the androgen receptor. This affinity has been demonstrated for selected compounds using the human receptor. The description below describes how the assay was carried out.

Competitive binding analysis was performed on baculovirus/Sf9 generated hAR extracts in the presence or absence of different concentrations of test agent and a fixed concentration of $^3$H-dihydrotestosterone ($^3$H-DHT) as tracer. This binding assay method is a modification of a protocol previously described (Liao S., et. al. *J. Steroid Biochem.* 20:11-17 1984). Briefly, progressively decreasing concentrations of compounds are incubated in the presence of hAR extract (Chang et al. *P.N.A.S.* Vol. 89, pp. 5546-5950,1992), hydroxylapatite, and 1 nM $^3$ H-DHT for one hour at 4° C. Subsequently, the binding reactions are washed three times to completely remove excess unbound $^3$ H-DHT. hAR bound $^3$H-DHT levels are determined in the presence of compounds (=i.e competitive binding) and compared to levels bound when no competitor is present (=i.e. maximum binding). Compound binding affinity to the hAR is expressed as the concentration of compound at which one half of the maximum binding is inhibited. Table II below provides the results that were obtained for selected compounds (reported data is the mean of multiple tests as shown below)

TABLE II

| Example # | Structure | AR Binding IC₅₀ (nM) |
|---|---|---|
| 1 | 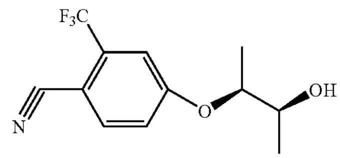 | 351 (c) |
| 2 | 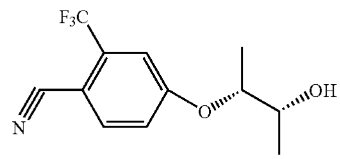 | 501 (c) |
| 3 | 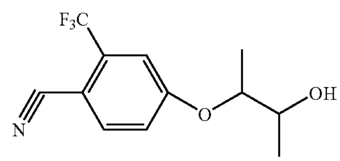 | 66 (b) |
| 4 | 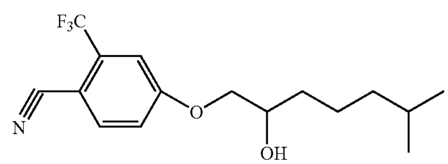 | 442 (a) |
| 5 | 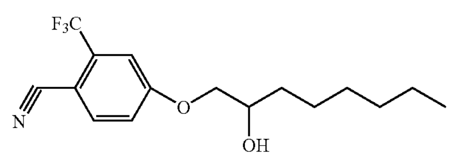 | 32 (a) |
| 6 | 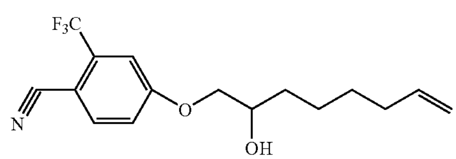 | 415 (a) |
| 7 | 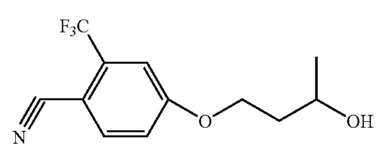 | 274 (a) |
| 8 | 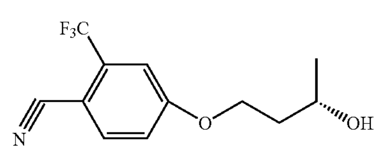 | 213 (a) |

TABLE II-continued

| Example # | Structure | AR Binding IC$_{50}$ (nM) |
|---|---|---|
| 9 | 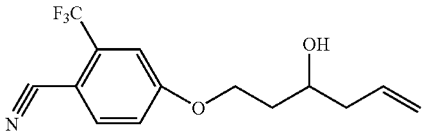 | 268 (a) |
| 10 | 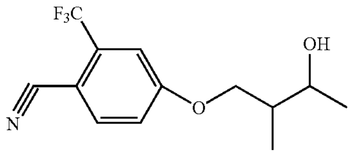 | 70 (a) |
| 11 | 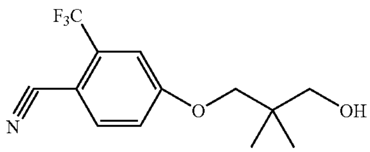 | 706 (a) |
| 12 | 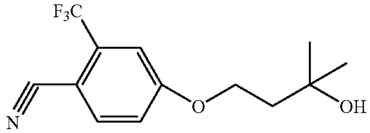 | 27 (a) |
| 13 | 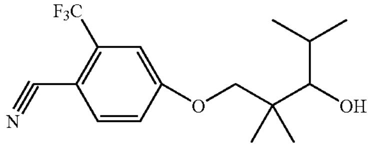 | 442 (a) |
| 14 | 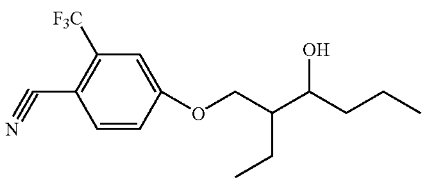 | 260 (b) |
| 15 | 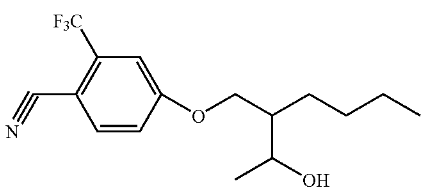 | 210 (a) |
| 16 | 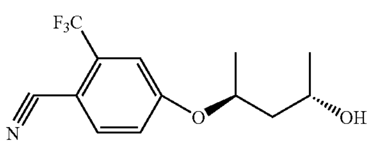 | 6 (a) |
| 17 | 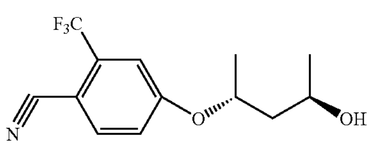 | 107 (a) |
| 18 | | 74 (a) |
| 19 | | 505 (a) |
| 20 | | 243 (a) |
| 21 | | 808 (a) |
| 22 | | 185 (a) |
| 23 | | 41 (c) |
| 24 | | 632 (c) |
| 25 | | 504 (a) |
| 26 | | 777 (a) |

TABLE II-continued

| Example # | Structure | AR Binding IC$_{50}$ (nM) |
|---|---|---|
| 27 | [Structure: 2-chloro-4-(3-hydroxy-2,2-dimethyl-4-methylpentyloxy)benzonitrile] | 63 (c) |
| 28 | [Structure: 2-chloro-4-(5-hydroxyhexan-2-yloxy)benzonitrile] | 49 (a) |
| 29 | [Structure: 2-chloro-4-(3-hydroxypropoxy)benzonitrile] | 394 (a) |
| 30 | [Structure: 2-chloro-4-(4-hydroxybutoxy)benzonitrile] | 99 (a) |
| 31 | [Structure: 2-chloro-4-(1-hydroxymethyl-allyloxy)benzonitrile] | 156 (a) |

(a) - mean of two tests
(b) - mean of three tests
(c) - mean of four tests

EXAMPLE 33

The compounds ability to antagonize the effects of androgen on the androgen receptor were determined in a whole cell assay as described immediately below.

Experimental Procedure for AR Antagonist Cell Assay

Cell line: MDA-MB453-MMTV clone 54-19. This cell line is a stable transfected cell line with MDA-MB453 cell background (a human breast tumor cell line expressing androgen receptor). A MMTV minimal promoter containing ARE was first cloned in front of a firefly luciferase reporter gene. Then the cascade was cloned into transfection vector pUV120puro. Electroporation method was used for transfecting MDA-MB-453 cell. Puromycin resistant stable cell line was selected.

Cell Culture Media and Reagents:

Culture medium: DMEM (high glucose, Gibco cat #: 11960-044), 10% FBS, and 1% L-glutamine Plating medium: DMEM (phenol red free), 10% charcoal treated HyClone serum, 1% L-glutamine Assay medium: DMEM (phenol red free), 1% charcoal treated HyClone serum, 1% L-glutamine, and 1% penicillin/streptomycin 3X luciferase buffer: 2% beta-mercaptoethanol, 0.6% ATP, 0.0135% luciferin in cell lysis buffer Assay Procedure:
1. Cells are maintained in culture medium, splitting cells when they reach 80-90% confluence
2. To test compounds, 10,000 cells/well are plated to opaque 96 cell culture plate in 100 ul/well plating medium, culture for overnight at 37° C. in cell culture incubator
3. Carefully remove plating medium, then add 80 ul/well of pre-warmed assay medium, add 10 ul/well testing compound (final concentration at) 1000 nM, 200 nM, 40 nM, 8 nM, 1.6 nM, and 0.32 nM), incubate at 37° C. for 30 minutes
4. Add 10 ul/well freshly prepared DHT (final concentration at 100 pM) to each well, incubate at 37° C. for 17 hr (overnight)
5. Add 50 ul/well 3X luciferase buffer, incubate at room temperature for 5 minutes, then count on Luminometer The fold induction over background by 100 pM DHT in the absence of testing compounds is standardized as 100% and experimental result is expressed as percentage of inhibition by testing compounds.

The results are described below in Table III. The results are reported as the mean of multiple tests as described below (the numbers of tests are indicated in the footnote). N.D. denotes that the compound was not tested.

TABLE III

| Example # | Structure | AR Cell IC50 (nM) |
|---|---|---|
| 1 | [Structure: 2-trifluoromethyl-4-(3-hydroxybutan-2-yloxy)benzonitrile] | N.D. |
| 2 | [Structure: 2-trifluoromethyl-4-(3-hydroxybutan-2-yloxy)benzonitrile stereoisomer] | N.D. |
| 3 | [Structure: 2-trifluoromethyl-4-(3-hydroxybutan-2-yloxy)benzonitrile] | >1000 (a) |
| 4 | [Structure: 2-trifluoromethyl-4-(2-hydroxy-6-methylheptyloxy)benzonitrile] | >1000 (a) |
| 5 | [Structure: 2-trifluoromethyl-4-(2-hydroxyheptyloxy)benzonitrile] | 509 (a) |

TABLE III-continued

| Example # | Structure | AR Cell IC50 (nM) |
|---|---|---|
| 6 | F3C-/CN-phenyl-O-CH2-CH(OH)-CH2CH2CH2CH=CH2 | 662 (a) |
| 7 | F3C-/CN-phenyl-O-CH2CH2-CH(OH)-CH3 | >1000 (c) |
| 8 | F3C-/CN-phenyl-O-CH2CH2-CH(OH)-CH3 (S) | >1000 (a) |
| 9 | F3C-/CN-phenyl-O-CH2CH2-CH(OH)-CH2-CH=CH2 | N.D. |
| 10 | F3C-/CN-phenyl-O-CH2-CH(CH3)-CH(OH)-CH3 | 274 (a) |
| 11 | F3C-/CN-phenyl-O-CH2-C(CH3)2-CH2OH | N.D. |
| 12 | F3C-/CN-phenyl-O-CH2CH2-C(CH3)2-OH | 269 (a) |
| 13 | F3C-/CN-phenyl-O-CH2-C(CH3)2-CH(OH)-CH(CH3)2 | N.D. |
| 14 | F3C-/CN-phenyl-O-CH2-CH(C2H5)-CH(OH)-CH2CH2CH3 | 794 (a) |
| 15 | F3C-/CN-phenyl-O-CH2-CH(C4H9)-CH(OH)-CH3 | 124 (a) |
| 16 | F3C-/CN-phenyl-O-CH(CH3)-CH2-CH(OH)-CH3 | >1000 (a) |
| 17 | F3C-/CN-phenyl-O-CH(CH3)-CH2-CH(OH)-CH3 | 807 (a) |
| 18 | F3C-/CN-phenyl-O-CH2CH2CH2CH2-OH | 398 (a) |
| 19 | F3C-/CN-phenyl-O-CH2CH2CH2-CH(OH)-CH3 | >1000 (a) |
| 20 | F3C-/CN-phenyl-O-CH2CH2CH2-CH(OH)-CH2CH2CH3 | 498 (a) |
| 21 | F3C-/CN-phenyl-O-CH(C3H7)-CH2CH2CH2-OH | N.D. |
| 22 | F3C-/CN-phenyl-O-CH(CH3)-CH2-CH(OH)-CH3 | >1000 (a) |

TABLE III-continued

| Example # | Structure | AR Cell IC50 (nM) |
|---|---|---|
| 23 | (4-cyano-3-(trifluoromethyl)phenyl ether with branched alkyl diol) | 132 (N = 10) |
| 24 | (4-cyano-3-(trifluoromethyl)phenyl ether with pentanol chain) | >1000 (a) |
| 25 | (4-cyano-3-(trifluoromethyl)phenyl ether with methyl-substituted pentanol) | 838 (N = 1) |
| 26 | (4-cyano-3-(trifluoromethyl)phenyl ether with methyl-branched alcohol) | N.D. |
| 27 | (2-chloro-4-cyanophenyl ether with gem-dimethyl hydroxy isopropyl chain) | 0.04 (a) |
| 28 | (2-chloro-4-cyanophenyl ether with methyl-branched diol chain) | 263 (a) |
| 29 | (2-chloro-4-cyanophenyl ether with propanol chain) | N.D. |
| 30 | (2-chloro-4-cyanophenyl ether with butanol chain) | N.D. |
| 31 | (2-chloro-4-cyanophenyl ether with allyl hydroxymethyl chain) | N.D. |

(a) - mean of two tests
(b) - mean of three tests
(c) - mean of four tests

EXAMPLE 34

Animal Model for Androgenetic Alopeica

As described above, alopecia is a problem that medical science has devoted considerable resources to. As with any disease process, animal models have been developed to allow scientists to screen compounds for their potential relative efficacy. Those compounds showing the greatest efficacy in these animal models are considered for further study in humans. Two different animal models have been developed to date for alopecia. The first is the telogen conversion assay, which uses female C3H/HeN mice. The second model uses stump-tailed macaques, which are monkeys that suffer from androgenetic alopecia.

The telogen conversion assay measures the potential of a compound to convert the resting stage of the hair growth cycle ("telogen") to the active stage of the hair growth cycle ("anagen") in mice. This assay takes advantage of the fact that the fur (i.e. hair) of 7-week-old C3H/HeN mice is in the telogen phase. This phase continues until about 75 days of age. In this assay, selected areas of the mice are shaved, contacted with a test agent, or a control, and the difference in the rate of hair growth is measured (i.e. induction of the anagen phase). The first sign of anagen is the darkening of skin color as melanocytes in the follicles start to synthesize melanin, in preparation for the production of pigmented hairs. This model has a number of advantages. This includes the ready availability of female CH3HeN mice, the ability to screen large numbers of compounds quickly, and the ease of housing and handling such animals.

The primary disadvantage of this model is its lack of androgenetic dependency. While the exact cause of human baldness is not known, it is well documented that androgens induce a regression of hair follicles in the scalp. This post adolescent regressive change is a fundamental cause of male pattern baldness, (i.e. "androgenetic alopecia). This phenomenon occurs in both men and women who have inherited the genetic trait for alopecia, as mentioned previously. For a more detail discussion of the effects of androgens on human scalps, the readers attention is directed to Trueb, RM, Molecular Mechanisms of Androgenic Alopecia, *Exp. Gerontology*, 2002, 27:981-990.

Researchers looked for other animals whose hair growth was similar to that of humans. These lead researchers to stump-tailed macaques. These primates also suffer from androgenetic alopecia. Essentially all post adolescent macaques, in both sexes, exhibit the development of baldness. Like the development of male pattern baldness in humans, androgens are an indispensable triggering factor in macaque baldness. Thinning of the frontal scalp hairs begins to appear around the same age (4 years) when serum levels of testosterone become drastically elevated in male animals. Although the elevation of testosterone in females is approximately one tenth that of the male level, there is no difference in the incidence and the age of onset of baldness between male and female stump-tailed macaques. Topical application of anti-androgens have reversed this baldness in animals of both sexes (Pan, H J et al, Evaluation of RU58841 as an anti-androgen in prostate PC3 cells and a topical anti-alopecia agent in the bald scalp of stump tailed macaques. *Endocrine* 1998; 9:39-43).

While this model is a significant improvement over the telogen conversion assay as a model for human baldness, it suffers from a number of practical disadvantages. The macaques are expensive, relatively rare, labor intensive to maintain, and require long wash out periods between testing. Thus, the macaque is not a practical model for screening large numbers of compounds It has been discovered that male C3H/HeN mice may be used in the telogen conversion assay, when evaluating anti-androgen test compounds. Thus, the model relates to a modi fication of the existing telogen conversion assay. Male C3H/HeN mice approximately 7 weeks old are utilized. These animals are also uniformly in telogen, like their female counterparts. However, once shaven, the androgens inherently present in these male mice inhibit the conversion of the hair follicles to the anagen phase. An anti-androgen will block this androgenic effect and the follicles will convert to anagen, like their female counterparts.

EXAMPLE 34 A

The compound described in Example 23, (1S,4S)-4-(4-Hydroxy-1-methyl pentyloxy)-2-trifluoromethyl-benzonitrile was submitted for further testing utilizing the modified telogen conversion assay, described above. The testing was carried out in the following manner.

Male C3H/HeN mice, 6 to 7 weeks old (Charles River Laboratories, Raleigh, N.C.) were used for the study. Fur was clipped from the dorsal region of the mice prior to initiation of the study. Only mice with pink skin, a visual indication of the telogen phase, were selected for inclusion in the study.

The test compound was dissolved in a vehicle consisting of propylene glycol (30%) and ethanol (70%) to achieve a concentration of either 0.2% w/v, 0.5% w/v, 1% w/v or 3% w/v. The relevant dose was applied topically to the clipped dorsal region of the mice in one test group (7-10 mice) in a volume of 20 µl/cm$^2$. A third group of animals received only the vehicle to serve as a control. Treatments were applied twice daily for 4 weeks.

The treatment area was observed and graded every other day for signs of hair growth. The hair growth response was quantified by recording, for each animal, the day on which signs of hair growth first appeared over the treated area. The first sign of anagen was the darkening of skin color as melanocytes in the follicles started to synthesize melanin in preparation for the production of pigmented hairs. The mice were observed for 35 days or longer. The percentage of mice showing signs of hair growth in both the treatment group and the control group is graphically depicted in FIG. 1. The compound of Example 23, when tested at a concentration of 1%, produced substantial hair growth by stimulating the induction of anagen in the test animals. The rate of hair growth in the 5% test group did not exceed that of the vehicle control group.

EXAMPLE 34 B

The product of Example 27, 2-chloro-4-(3-hydroxy-2,2,4-trimethyl-pentyloxy)-benzonitrile, was submitted for testing utilizing the modified telogen conversion assay, described above. The testing was carried out in the same manner as Example 37 A, at a test concentration of 3% w/v. The rate of hair growth for the test group did not exceed that of the vehicle control.

EXAMPLE 35

Animal Model for Inhibition of Sebum Production

Luderschmidt et al describes an animal model for testing whether compounds are capable of modulating sebum secretion. Arch. Derm. Res. 258, 185-191 (1977). This model uses male Syrian hamsters, whose ears contain sebaceous glands. Selected compounds produced above were screened in this model.

Testing for sebum inhibition was carried out in the following manner. Male Syrian hamsters aged 9 to 10 weeks were introduced into the laboratory environment and acclimated for 2 weeks prior to use in the study. Each group consisted of 5 animals and were run in parallel with vehicle and positive controls. Prior to administration, 30mg of each compound was dissolved in 1 mL of Universal solvent (ethanol/propylene glycol (70/30%v/v) to achieve a final concentration of 3 w/v%.

Animals were dosed topically twice daily, five days a week, for 4 weeks. Each dose consisted of 25 micro liters of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at −80° C. under nitrogen until HPLC analysis. In addition to ear samples, an aliquot of each drug and vehicle (at least 250 ul) was also stored at −80° C. for inclusion in the HPLC analysis.

HPLC analysis was carried out on an extract of the tissue sample. Tissue samples were contacted with 3ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at 37° C., under nitrogen, for approximately 1 hour, and then lyophilized for approximately 48 hours. The samples were then removed from the lyophilizer and each vial was reconstituted with 600 µl of solvent A (trimethylpentane/tetrahydrofuran (99:1). The samples were then recapped and vortexed for 5 minutes.

200 µl of each sample was then transferred to a pre-labeled 200 µl HPLC vial with 200 µL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at 30° C. by the Agilent column heater unit. The HPLC autosampler was programmed to maintain the sample temperature at 20° C. throughout the run.

10 uL of each sample was injected in triplicate into the column. Two solvents were used for the solvent gradient. Solvent A was an admixture of trimethylpentane and tetrahydrofuran (99:1). Solvent B was ethylacetate. The gradient utilized is described in the table below:

| Time (min) | Solv A (%) | Solv B (%) | Flow (mL/min) |
| --- | --- | --- | --- |
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at 45° C. with a gain of 5, and $N_2$ pressure maintained at 3.1 bar. Analog signal obtained by the instrument was sent to the Agilent A/D interface module where it was converted to a digital output. The conversion was based on a 10000 mAU/volt set point and the data rate was set at 10 Hz (0.03 min). The resulting digital output was then feed into the Agilent ChemStation software for integration of the peak area.

The results of the HPLC analysis are reported below in Table IV. The results are reported as the reduction in cholesterol ester (CE) and wax ester (WE) production, when compared to the vehicle control.

| Compound | Structure | % Reduction in CE | % Reduction in WE | Sum CE + WE |
| --- | --- | --- | --- | --- |
| Example 23 | 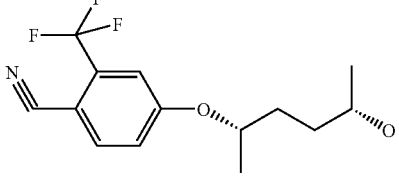 | 67% | 87% | 154% |
| Example 15 | 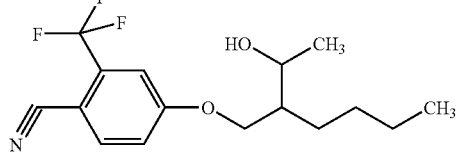 | 54% | 74% | 128% |

Columns 1 and 2 identify the compound by structure and Example number. Columns 3 through 5 show the effect the compounds had on the -reduction of sebum components (CE and WE). The results are expressed as the difference from the vehicle control. A positive number reflects a decrease in the production of the sebum component being measured, i.e. cholesterol ester (CE) or wax ester (WE).

Column 3 shows the compounds ability to reduce the amount of cholesterol ester in the sebum sample. Column 4 shows the effect the compound had on the generation of wax ester. Wax esters are specific markers of the sebaceous glands and are not appreciably detected in any other layer of the skin. Wax ester is the largest component of sebum (approximately 25%). Thus reducing wax ester typically leads to significant reductions in sebum secretion. Column 5 is a summation of the results expressed in columns 3 and 4 (and is included to further elucidate relative differences in activity). As shown in Table IV, the androgen modulators of Formula I significantly decreased the production of both cholesterol ester and wax ester.

What is claimed is:

1. 4-(4-Hydroxy-1-methyl-pentyloxy)-2-trifluoromethyl-benzonitrile, a pharmaceutically acceptable salt thereof, or a hydrate thereof.

2. (1S,4S)-4-(4-Hydroxy-1-methyl-pentyloxy)-2-trifluoromethyl-benzonitrile, a pharmaceutically acceptable salt thereof, are hydrate thereof.

3. A method for alleviating alopecia comprising the topical administration of an effective amount of a compound according to claim 2 to a human in need of such treatment.

4. A method for decreasing sebum secretion comprising the topical administration of an effective amount of a compound according to claim 2 to a human in need of such treatment.

5. A method for alleviating oily skin comprising the topical administration of an effective amount of a compound according to claim 2 to a human in need of such treatment.

6. A method for alleviating acne comprising the topical administration of an effective amount of a compound according to claim 2 to a human in need of such treatment.

7. A pharmaceutical composition comprising a compound according to claim 2 in admixture with one, or more, pharmaceutically acceptable excipients.

8. A topical pharmaceutical formulation comprising a compound according to claim 2 in admixture with a dermatologically acceptable carrier.

9. A kit comprising a compound according to claim 2 packaged for retail distribution which advises a consumer how to utilize the compound to alleviate a condition selected from the group consisting of acne, alopecia, and oily skin.

10. 4-(4-Hydroxy-1-methyl-pentyloxy)-2-trifluoromethyl-benzonitrile, or a salt thereof.

11. (1S,4S)-4-(4-Hydroxy-1-methyl-pentyloxy)-2-trifluoromethyl-benzonitrile, or a salt thereof.

* * * * *